United States Patent
Kim et al.

(10) Patent No.: US 10,182,918 B2
(45) Date of Patent: Jan. 22, 2019

(54) INTERSPINOUS DYNAMIC IMPLANT

(71) Applicants: SOLCO BIOMEDICAL CO., LTD., Pyeongtaek-si (KR); Hyeun-Sung Kim, Daejeon (KR)

(72) Inventors: Hyeun-Sung Kim, Daejeon (KR); Hong-Won Yoon, Gunpo-si (KR)

(73) Assignees: SOLCO BIOMEDICAL CO., LTD., Pyeongtaek-si (KR); Hyeun-Sung Kim, Daejeon (KR)

( * ) Notice: Subject to any disclaimer, the term of this patent is extended or adjusted under 35 U.S.C. 154(b) by 0 days.

(21) Appl. No.: 15/520,142

(22) PCT Filed: Oct. 19, 2015

(86) PCT No.: PCT/KR2015/011023
§ 371 (c)(1),
(2) Date: Apr. 19, 2017

(87) PCT Pub. No.: WO2016/064148
PCT Pub. Date: Apr. 28, 2016

(65) Prior Publication Data
US 2017/0325965 A1    Nov. 16, 2017

(30) Foreign Application Priority Data
Oct. 20, 2014    (KR) .................. 10-2014-0142126

(51) Int. Cl.
*A61B 17/70*    (2006.01)
*A61F 2/44*    (2006.01)

(52) U.S. Cl.
CPC ............ *A61F 2/4405* (2013.01); *A61B 17/70* (2013.01); *A61B 17/7065* (2013.01);
(Continued)

(58) Field of Classification Search
CPC .. A61F 2/4405; A61F 2002/443; A61F 2/441; A61B 17/70; A61B 17/7065; A61B 17/70684
(Continued)

(56) References Cited

U.S. PATENT DOCUMENTS

| 5,645,599 A * | 7/1997 | Samani | A61B 17/7062 |
| | | | 606/248 |
| 8,142,479 B2 * | 3/2012 | Hess | A61B 17/7065 |
| | | | 606/248 |

(Continued)

FOREIGN PATENT DOCUMENTS

| CN | 101316558 A | 12/2008 |
| CN | 102512231 A | 6/2012 |

(Continued)

OTHER PUBLICATIONS

PCT International Search Report and Written Opinion dated Feb. 3, 2016 from corresponding Application No. PCT/KR2015/011023.

*Primary Examiner* — Pedro Philogene
(74) *Attorney, Agent, or Firm* — Dilworth IP, LLC

(57) ABSTRACT

The present invention relates to an interspinous dynamic implant. Provided is an interspinous dynamic implant comprising: an upper plate which adheres to an upper spinous process; a lower plate which adheres to a lower spinous process; a movable part, coupled between the front portion of the upper plate and the front portion of the lower plate, for enabling the upper plate and the lower plate to move upwards, downwards, left and right within a certain range according to the movement of spinous processes; an upper spinous process coupling means for tightly coupling the upper plate to the upper spinous process; and a lower spinous process coupling means for tightly coupling the lower plate to the lower spinous process.

14 Claims, 8 Drawing Sheets

(52) U.S. Cl.
CPC ............ *A61B 17/7068* (2013.01); *A61F 2/44* (2013.01); *A61F 2/441* (2013.01); *A61F 2002/443* (2013.01)

(58) Field of Classification Search
USPC .......... 606/246–279, 86 A; 623/17.11–17.16
See application file for complete search history.

(56) References Cited

U.S. PATENT DOCUMENTS

| | | | | |
|---|---|---|---|---|
| 8,430,911 | B2* | 4/2013 | Chin | ................. A61B 17/7065 606/248 |
| 9,039,742 | B2* | 5/2015 | Altarac | ................ A61B 17/025 606/248 |
| 2016/0296338 | A1* | 10/2016 | Kim | .......................... A61F 2/44 |

FOREIGN PATENT DOCUMENTS

| | | | | |
|---|---|---|---|---|
| JP | 2012513882 | A | 6/2012 | |
| JP | 20130004482 | U | 7/2013 | |
| KR | 10-0954574 | B1 | 4/2010 | |
| KR | 10-2010-0080908 | A | 7/2010 | |
| KR | 10-1030462 | B1 | 4/2011 | |
| KR | 20120021276 | A | 3/2012 | |
| KR | 20-2013-0004482 | U | 7/2013 | |
| KR | 2020130004482 | * | 7/2013 | ........... A61F 2/4405 |
| KR | 10-2013-0102987 | A | 9/2013 | |
| KR | 10-1346095 | B1 | 12/2013 | |
| KR | 10-1397192 | B1 | 5/2014 | |

* cited by examiner

[Fig. 1]
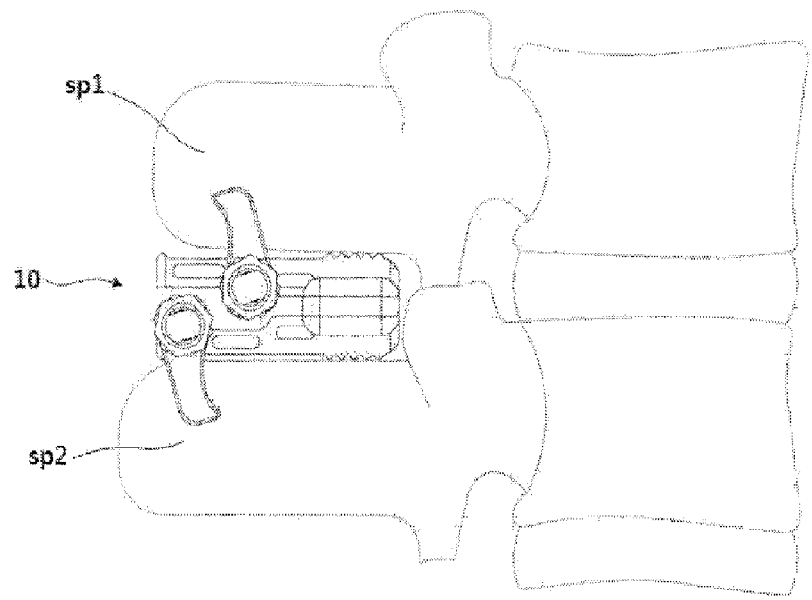
[Fig. 2]
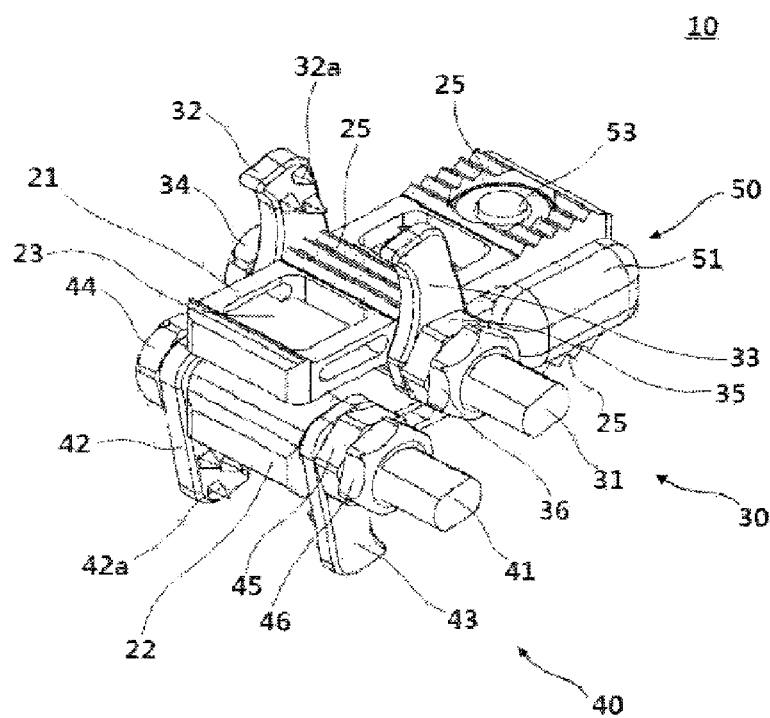

[Fig. 3]
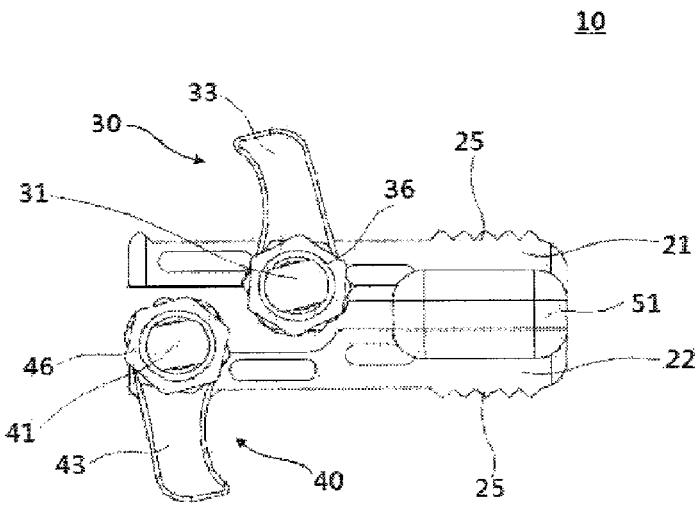
[Fig. 4]
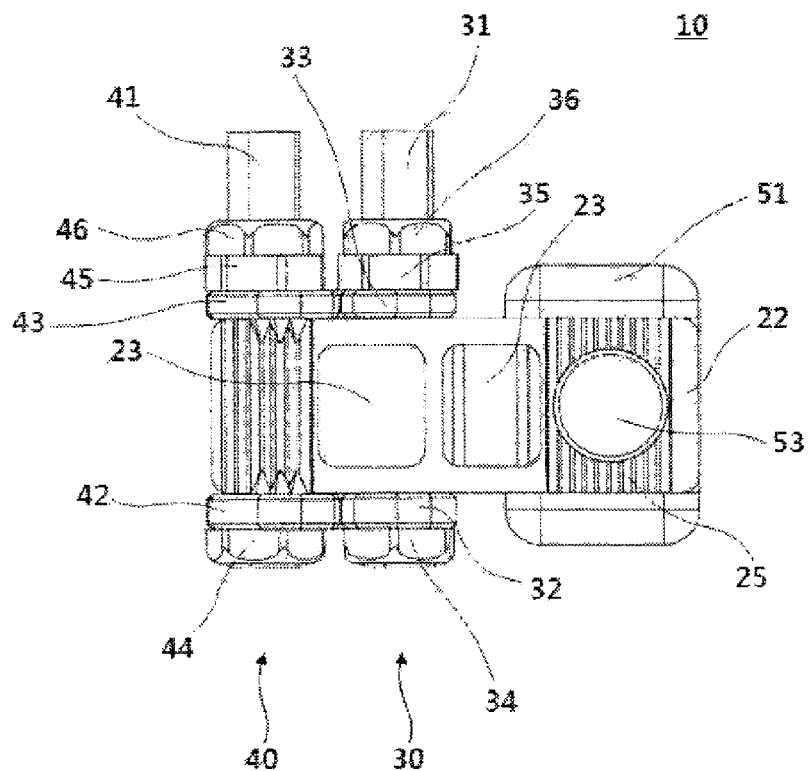

[Fig. 5]
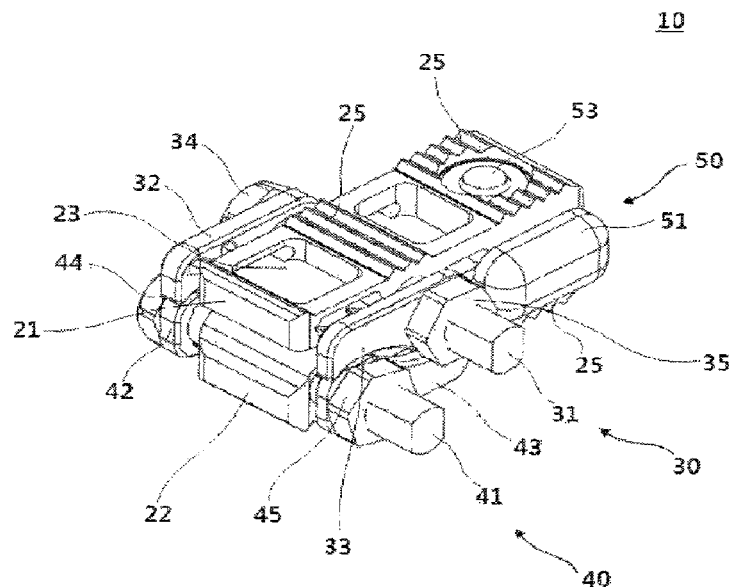
[Fig. 6]
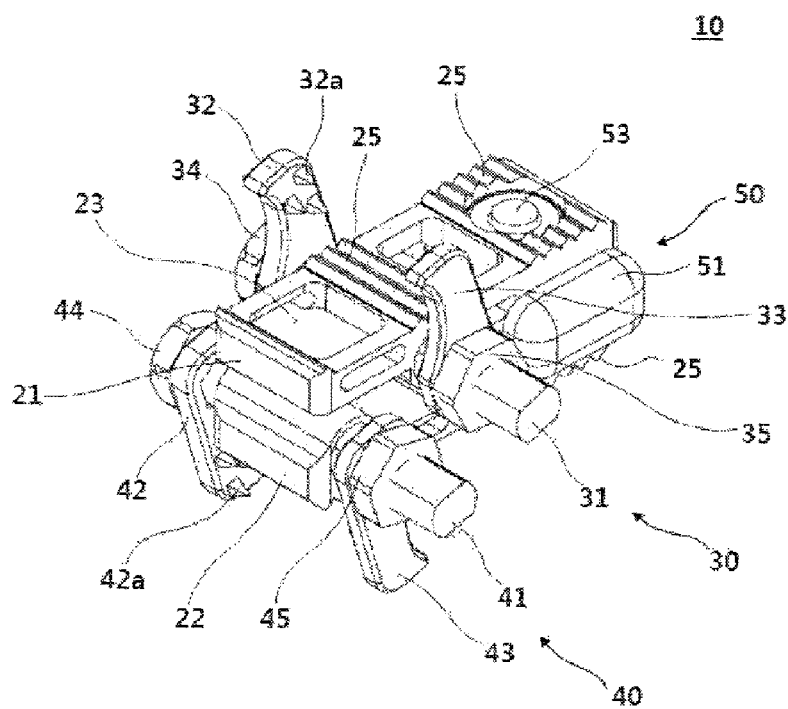

[Fig. 7]
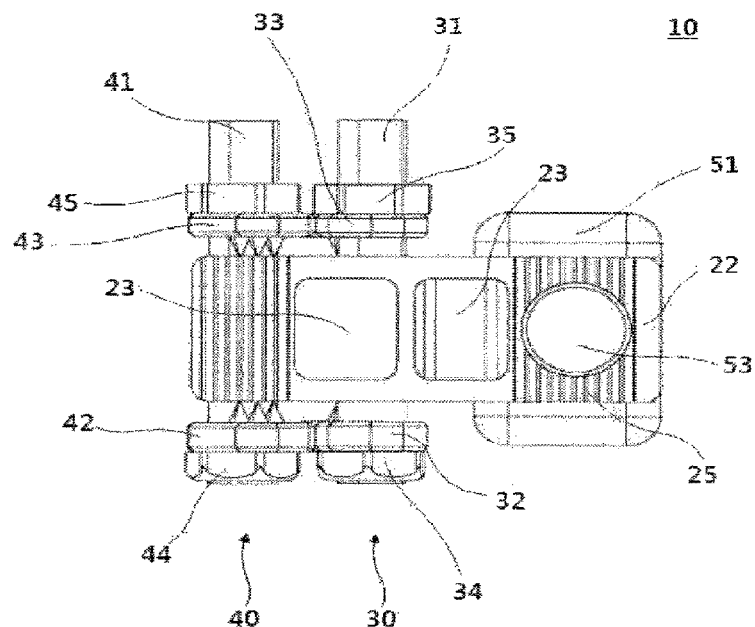
[Fig. 8]
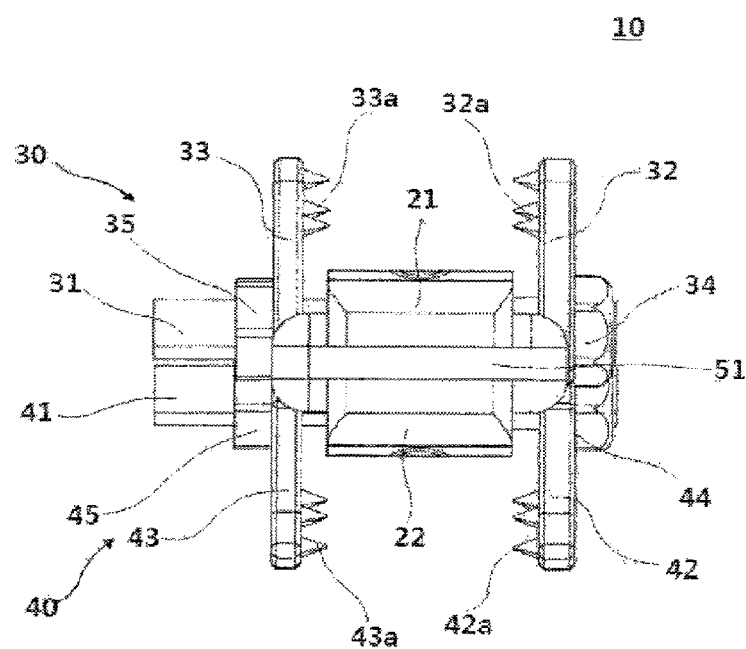

[Fig. 9]
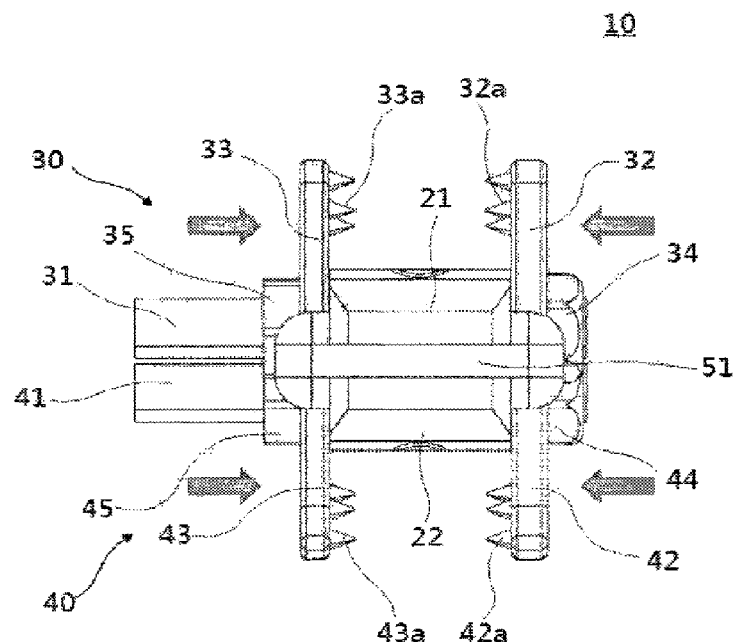
[Fig. 10]
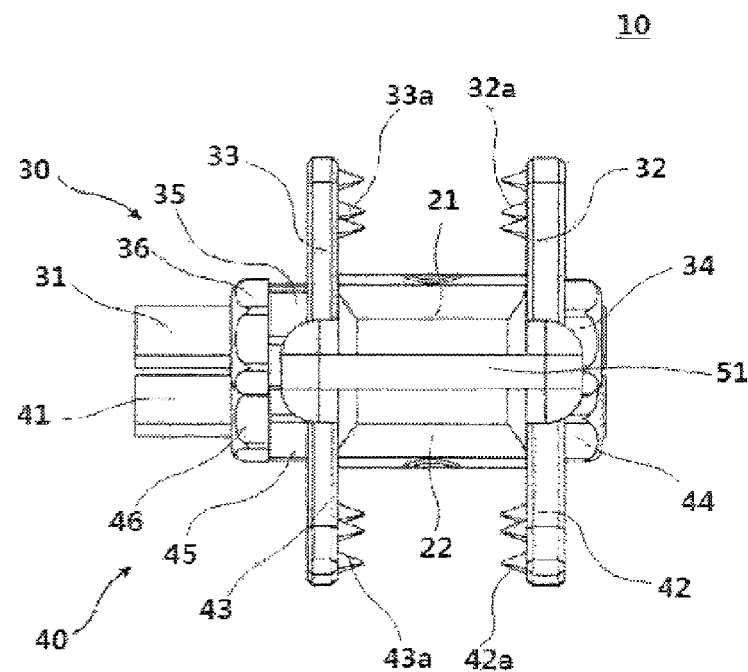

[Fig. 11]
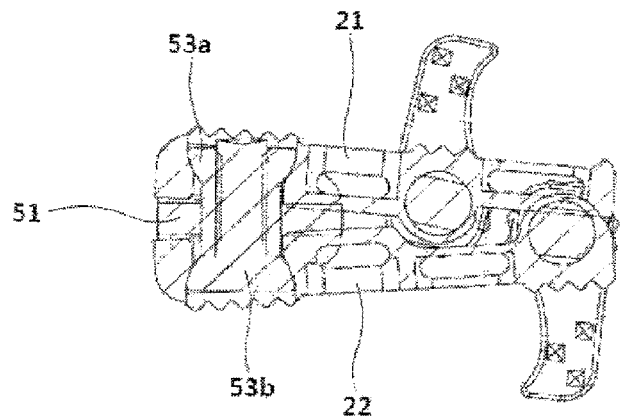
[Fig. 12]
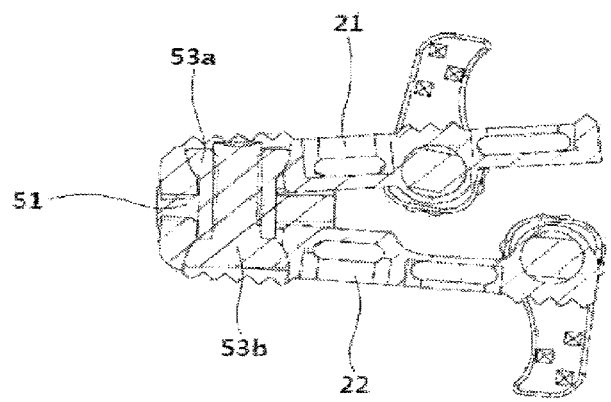
[Fig. 13]
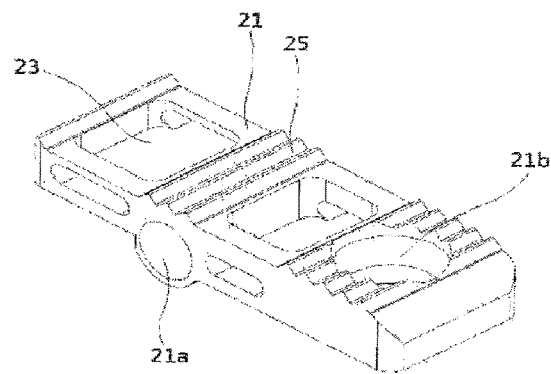

[Fig. 14]
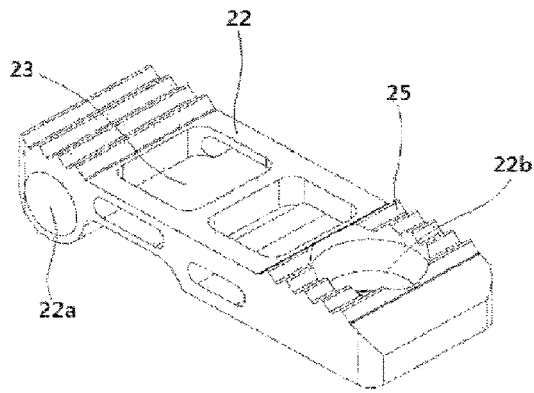
[Fig. 15]
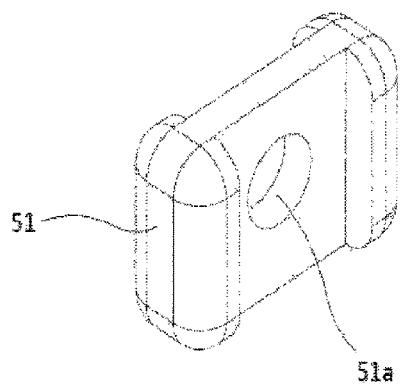
[Fig. 16]
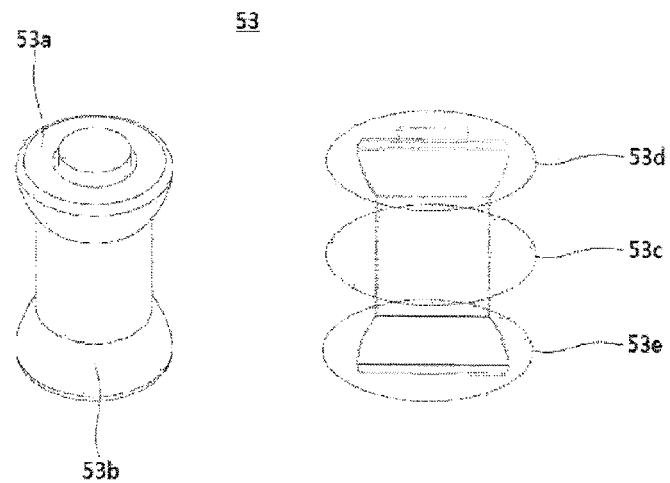
(a)  (b)

[Fig. 17]
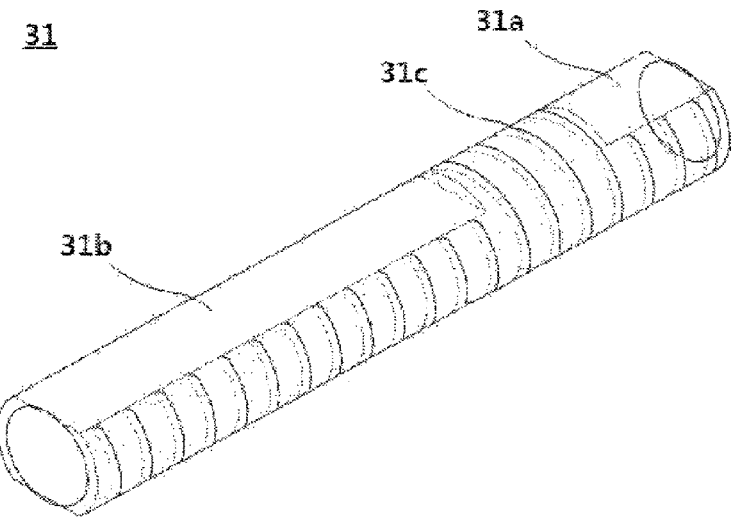
[Fig. 18]
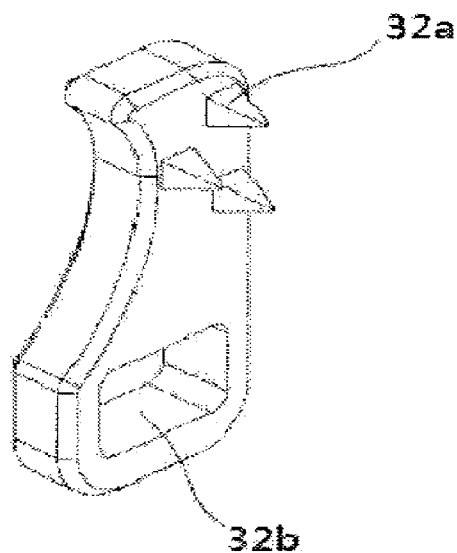

INTERSPINOUS DYNAMIC IMPLANT

BACKGROUND OF THE INVENTION

Field of the Invention

The present invention relates to an interspinous dynamic implant and, more particularly, to an interspinous dynamic implant inserted between adjacent spinous processes in order to treat spinal canal stenosis which is generated because a spinal canal, nerve root canal or intervertebral foramen at the center of a spine is narrowed.

Related Art

A spinal canal is a passage through which a vertebral nerve that is connected to the brain of the head, that transfers a signal generated by the brain to an arm and leg, and that functions as an "electric wire" passes. Holes at the rear of respective vertebrae are connected up and down to form a tunnel, and nerves continue from the brain to the arm and leg through the tunnel.

Spinal canal stenosis is a disease in which a passage through which such a vertebral nerve passes is narrowed to presses the nerve. The most commonly generated degenerative stenosis is generated because as a vertebra experiences an aging process, a disc (intervertebral disc) that has caused a degenerative change at the front pops out and presses a nerve, a ligamentum flavum that surrounds the nerve becomes thick and hard-set to press the nerve at the back, a facet joint located at the back of a spinal canal is swollen, and a vertebral nerve is pressed by a bone (osteophyte) abnormally grown by the friction of the vertebra.

Recently, in order to treat such spinal canal stenosis, an implant inserted between adjacent spinous processes is widely used. However, a conventional implant has problems in that a spinous process is damaged because upper and lower spinous processes are not fused and are separately moved, thus, a vertebra moves for a long period of time and also the implant escapes between the spinous processes.

Furthermore, an upper plate and a lower plate that form the implant move upward or downward from the upper spinous process and the lower spinous process and thus can provide some elastic force, but the implant has a limit that it does not naturally move along the leftward and rightward movements of the upper spinous process and the lower spinous process in addition on the upward and downward movements.

Furthermore, there are problems in that a long operation time is taken because a ligament must be cut in the rear of the back and the implant must be inserted in order to insert the implant between the spinous processes and the time taken for a patient to recover after the operation is long.

Furthermore, there is a problem in that the implant is not coupled to the upper and lower spinous processes perfectly and stably because a wing portion coupled to the upper and lower spinous processes is not configured to be adjusted according to the thickness of the spinous process after the implant is inserted between the spinous processes.

There are Korean Patent No. 10-1346095 and Korean Patent Application Publication No. 10-2010-0080908 as prior art documents.

SUMMARY OF THE INVENTION

The present invention has been invented to improve the problems, and an object of the present invention is to provide an interspinous dynamic implant, which can maintain the space between an upper spinous process and a lower spinous process because the implant is inserted between adjacent spinous processes to provide an elastic force to the upper spinous process and the lower spinous process and which can be integrated with the upper and lower spinous processes and moved therewith.

Furthermore, an object of the present invention is to provide an interspinous dynamic implant which can move along with an upward or downward or leftward or rightward movement of the upper spinous process and the lower spinous process.

Furthermore, an object of the present invention is to provide an interspinous dynamic implant capable of a minimum invasion procedure because wings are rotated and fastened using a tool after the implant is inserted on the side of spinous processes without using a method of inserting the implant at the rear of the spinous process.

Furthermore, an object of the present invention is to provide an interspinous dynamic implant in which an upper wing and a lower wing are coupled to a spinous process perfectly and stably by fastening the wings on both sides of the spinous process after the implant is inserted between adjacent spinous processes.

An interspinous dynamic implant of the present invention for achieving the objects includes an upper plate closely attached to an upper spinous process; a lower plate closely attached to a lower spinous process; a movable unit coupled between the front portion of the upper plate and the front portion of the lower plate to enable the upper plate and the lower plate to move upward or downward or leftward or rightward within a specific range in response to a movement of the spinous process; upper spinous process coupling means closely coupling the upper plate to the upper spinous process; and lower spinous process coupling means closely coupling the lower plate to the lower spinous process.

Furthermore, one or more osseointegration holes may be formed in at least one of the upper plate and the lower plate so that the at least one plate is fused with adjacent spinous processes.

Furthermore, a plurality of fixing protrusions may be formed in at least one of a top surface of the upper plate and a bottom surface of the lower plate so that the fixing protrusions are fused with adjacent spinous processes.

Furthermore, the movable unit may include a cushion unit of an elastic material which is located between the upper plate and the lower plate, which has a circular through hole formed at the center of the cushion unit, and which has side portions closely attached to both sides of the upper plate and the lower plate; and a coupling unit of a dumbbell shape which couples the upper plate, the cushion unit and the lower plate sequentially through a through hole formed to penetrate the upper plate from a top surface of the front portion of the upper plate to a bottom surface, a through hole formed in the cushion unit of the elastic material, and a through hole formed to penetrate the lower plate from a top surface of the front portion of the lower plate to a bottom surface.

Furthermore, the cushion unit of the elastic material may have an H form.

Furthermore, the coupling unit of the dumbbell shape may include a body unit located at the center of the coupling unit, a first coupling unit coupled to the through hole formed in the upper plate, and a second coupling unit coupled to the through hole formed in the lower plate. The outer surface of each of the first coupling unit and the second coupling unit may have a diameter increasing from the body unit to an outside, but forms a convex surface. The through holes formed in the upper plate and the lower plate may be formed to correspond to respective shapes corresponding to the first coupling unit and the second coupling unit.

Furthermore, the upper spinous process coupling means may be coupled to the upper plate, upward rotated, and then closely attached on both sides of the upper spinous process to be coupled to the upper spinous process. The lower spinous process coupling means may be coupled to the lower plate, downward rotated, and then closely attached on both sides of the lower spinous process to be coupled to the lower spinous process.

Furthermore, the upper spinous process coupling means may be upward rotated by a first rotation rod inserted into a through hole formed to penetrate the side of the upper plate and rotated with the upper plate, closely attached to both sides of the upper spinous process, and coupled to the upper spinous process. The lower spinous process coupling means may be downward rotated by a second rotation rod inserted into a through hole formed to penetrate the side of the lower plate and rotated with the lower plate, closely attached to both sides of the lower spinous process, and coupled to the lower spinous process.

Furthermore, an upper wing coupled to the first rotation rod through the first rotation rod may be upward rotated. A lower wing coupled to the second rotation rod through the second rotation rod may be downward rotated. The upper wing and the lower wing may be closely attached and mutually fastened on the first rotation rod and the second rotation rod, respectively, so a plurality of spinous process fixing spikes provided in the upper wing and a plurality of spinous process fixing spikes provided in the lower wing are embedded in the upper spinous process and the lower spinous process.

Furthermore, the through hole formed to penetrate the side of the upper plate and the through hole formed to penetrate the side of the lower plate may be formed at mutually dislocated locations so that the first rotation rod is provided more on a front side than the second rotation rod. The upper wing coupled to the first rotation rod may be upward rotated and the lower wing coupled to the second rotation rod may be downward rotated by rotating the first rotation rod and the second rotation rod in an identical direction.

Furthermore, oblong through holes to which the first rotation rod and the second rotation rod are coupled through the oblong through holes may be formed on the lower sides of the upper wing and the lower wing, respectively. A plurality of spinous process fixing spikes may be provided on the upper side of each of the upper wing and the lower wing. The outer surfaces of the first rotation rod and the second rotation rod may be formed in shapes capable of rotating the upper wing and the lower wing coupled to the first rotation rod and the second rotation rod through the first rotation rod and the second rotation rod.

Furthermore, the first rotation rod and the second rotation rod may have bolt forms. A bolt head may be located on one side of each of the upper plate and the lower plate. A bolt body may be exposed to the other side through the through hole. A left wing forming the upper wing may be coupled to a bolt body exposed between the bolt head and the upper plate. A left wing forming the lower wing may be coupled to a bolt body exposed between the bolt head and the lower plate. The right wing forming the upper wing and the right wing forming the lower wing may be coupled to the bolt body exposed to the other side.

Furthermore, the outer surfaces of the bolt bodies corresponding to portions coupled to the oblong through holes formed in the left wing and the right wing may include a plurality of faces flat cut in such a way as to rotate the left and right wings when the bolt bodies are rotated.

Furthermore, a fastening nut may be coupled to an outer bolt body of the right wing. When the fastening nut is fastened, the right wing may move in the direction of the left wing along the bolt body and the left wing may move in the direction of the right wing along the bolt body, so the left wing and the right wing are closely attached and fastened in a direction in which the left wing and the right wing face each other.

Furthermore, after the left and right wings are closely attached and fastened by the fastening nut, a fixing nut may be coupled to the outer bolt body of the fastening nut.

In accordance with the interspinous dynamic implant according to the present invention, there are advantages in that the space between the upper spinous process and the lower spinous process can be maintained because an elastic force is provided to the upper spinous process and the lower spinous process and a phenomenon in which the interspinous dynamic implant escapes between the upper spinous process and the lower spinous process can be prevented without damaging the spinous process because the implant is fused with the upper and lower spinous processes and moved therewith.

Furthermore, there are advantages in that a movement of the upper spinous process and the lower spinous process is more natural than that of a conventional implant and there is no burden on the spine because the implant can move along with an upward or downward or leftward or rightward movement of adjacent spinous processes.

Furthermore, there is an advantage in that a minimum invasion procedure is possible because the wings are rotated and fastened using a tool after the interspinous dynamic implant is inserted from the sides of the spinous processes.

Furthermore, there is an advantage in that the upper wing and the lower wing are stably coupled to the upper and lower spinous processes because the plurality of spikes included in the upper and lower wings are closely attached to both sides of the upper and lower spinous processes and embedded therein when the upper and lower wings are fastened on both sides of the upper and lower spinous processes after the interspinous dynamic implant is inserted between the adjacent spinous processes.

Furthermore, there is an advantage in that the interspinous dynamic implant can be inserted from the sides of the spinous processes as well as at the back of the spinous processes because the implant can be inserted between the spinous processes in the state in which the upper wing and the lower wing have been folded and thus the wings are not caught in the upper and lower spinous processes.

BRIEF DESCRIPTION OF THE DRAWINGS

FIG. 1 is a side view showing the state in which an interspinous dynamic implant according to the present invention has been inserted between spinous processes.

FIG. 2 is a perspective view showing the state in which the wings of the interspinous dynamic implant according to the present invention have been spread and then finally fixed.

FIG. 3 is a side view showing the state in which the wings of the interspinous dynamic implant according to the present invention have been spread and then finally fixed.

FIG. 4 is a plan view showing the state in which the wings of the interspinous dynamic implant according to the present invention have been spread and then finally fixed.

FIG. 5 is a perspective view showing the state when the interspinous dynamic implant according to the present invention is inserted between spinous processes after the wings of the implant is folded.

FIG. 6 is a perspective view showing the state in which the wings have been spread after the interspinous dynamic implant according to the present invention was inserted between spinous processes.

FIG. 7 is a plan view showing the state in which the wings have been spread after the interspinous dynamic implant according to the present invention was inserted between spinous processes.

FIG. 8 is a front view showing the state in which the wings have been spread after the interspinous dynamic implant according to the present invention was inserted between spinous processes.

FIG. 9 is a front view showing the state in which left and right wings have been fastened by fastening a fastening nut after the interspinous dynamic implant according to the present invention was inserted between spinous processes.

FIG. 10 is a front view showing the state in which the left and right wings of the interspinous dynamic implant according to the present invention have been fixed using a fixing nut after the left and right wings were fastened.

FIG. 11 is a side cross-sectional view showing the state in which the interspinous dynamic implant according to the present invention has been pressed by upper and lower spinous processes.

FIG. 12 is a side cross-sectional view showing the state in which the interspinous dynamic implant according to the present invention has been widened in response to a movement of the upper and lower spinous processes.

FIG. 13 is a perspective view of an upper plate.

FIG. 14 is a perspective view of a lower plate.

FIG. 15 is a perspective view of a cushion unit of an elastic material coupled between the upper plate and the lower plate.

FIG. 16 is a perspective view and front view of a coupling unit of a dumbbell shape which is coupled to the upper plate and the lower plate through them.

FIG. 17 is a perspective view of a rotation rod which is inserted into a through hole formed on the side of the spacer and rotated.

FIG. 18 is a perspective view of the wing including a plurality of spinous process fixing spikes.

DESCRIPTION OF EXEMPLARY EMBODIMENTS

Hereinafter, an embodiment according to the present invention is described in detail with reference to the accompanying drawings.

Referring to FIGS. 1 to 18, an interspinous dynamic implant (10) includes an upper plate (21) closely attached to an upper spinous process (sp1), a lower plate (22) closely attached to a lower spinous process (sp2), upper spinous process coupling means (30) which closely couples the upper plate (21) to the upper spinous process (sp1), lower spinous process coupling means (40) which closely couples the lower plate (22) to the lower spinous process (sp2), and a movable unit (50).

The movable unit (50) is coupled between the front portion of the upper plate (21) and the front portion of the lower plate (22), and enables the upper plate (21) and the lower plate (22) to move upward or downward or leftward or rightward within a specific range in response to a movement of the spinous processes (sp1 and sp2).

More specifically, the movable unit (50) includes a cushion unit (51) of an elastic material and a coupling unit (53) of a dumbbell shape.

Referring to FIG. 15, the cushion unit (51) of an elastic material is located between the upper plate (21) and the lower plate (22). A circular through hole (51a) is formed at the center of the cushion unit (51). Side portions of the cushion unit (51) are closely attached to both sides of the upper plate (21) and the lower plate (22). The cushion unit (51) of an elastic material may be made of a poly material and configured to have an H form. Accordingly, the central part of the cushion unit (51) is coupled between the front portions of the upper plate (21) and the lower plate (22), and the side portions thereof are closely attached to the sides of the upper plate (21) and the lower plate (22).

Referring to FIGS. 11 and 12, when the upper plate (21) and the lower plate (22) are closely attached or spaced apart in response to a movement of the upper and lower spinous processes (sp1 and sp2), the cushion unit (51) made of an elastic material can provide an elastic force while not putting stress on the movement of the upper plate (21) and the lower plate (22).

Referring to FIGS. 13, 14, 15 and 16, the coupling unit (53) of a dumbbell shape couples the upper plate (21), the cushion unit (51) and the lower plate (22) sequentially through a through hole (21b) formed to penetrate the upper plate (21) from the top surface of the front portion of the upper plate (21) to the bottom surface thereof, a through hole (51a) formed in the cushion unit (51) of an elastic material, and a through hole (22b) formed to penetrate the lower plate (22) from the top surface of the front portion of the lower plate (22) to the bottom surface thereof. FIG. 14 shows the state in which the lower plate (22) has been overturned so that the bottom surface of the lower plate (22) can be seen.

As shown in FIGS. 11 and 12, in the coupling unit (53) of a dumbbell shape, a dumbbell-shaped coupling unit (53a) of a nut form is coupled to a dumbbell-shaped coupling unit (53b) of a bolt form through the central axis of the dumbbell-shaped coupling unit (53b).

Referring to FIGS. 13, 14 and 16, the coupling unit (53) of a dumbbell shape includes a body unit (53c) located at the center of the coupling unit (53), a first coupling unit (53d) coupled to the through hole (21b) formed in the upper plate (21), and a second coupling unit (53e) coupled to the through hole (22b) formed in the lower plate (22). The outer surface of each of the first coupling unit (53d) and the second coupling unit (53e) has a diameter increasing from the body unit (53c) to the outside, but forms a convex surface. The through holes (21b and 22b) formed in the upper plate (21) and the lower plate (22) are formed to correspond to respective shapes corresponding to the first coupling unit (53d) and the second coupling unit (53e).

As shown in FIGS. 1 and 12, through such a configuration, the upper plate (21) and the lower plate (22) engaged with the coupling unit (53) can move leftward and rightward and can also move upward or downward within a specific range. In this case, when the upper plate (21) and the lower plate (22) move leftward or rightward, they move only within a specific range by the side portion of the cushion unit (51) of an elastic material.

The upper spinous process coupling means (30) is coupled to the upper plate (21) and upward rotated. Next, the upper spinous process coupling means (30) is closely attached on both sides of the upper spinous process (sp1) to be coupled to the upper spinous process (sp1). More specifically, the upper spinous process coupling means (30) is upward rotated by a first rotation rod (31) that is inserted into a through hole (21a) formed to penetrate the side of the upper plate (21) and that is rotated therein. Next, the upper spinous process coupling means (30) is closely attached on both sides of the upper spinous process (sp1), then, coupled to the upper spinous process (sp1).

The lower spinous process coupling means (40) is coupled to the lower plate (22) and downward rotated. Next, the lower spinous process coupling means (40) is closely attached on both sides of the lower spinous process (sp2) to be coupled to the lower spinous process (sp2). More specifically, the lower spinous process coupling means (40) is downward rotated by a second rotation rod (41) that is inserted into a through hole (22a) formed to penetrate the side of the lower plate (22) and that is rotated therein. Next, the lower spinous process coupling means (40) is closely attached on both sides of the lower spinous process (sp2) to be coupled to the lower spinous process (sp2).

Upper wings (32 and 33) coupled to the first rotation rod (31) through the first rotation rod (31) are upward rotated. Lower wings (42 and 43) coupled to the second rotation rod (41) through the second rotation rod (41) are downward rotated. The upper wings (32 and 33) and the lower wings (42 and 43) are closely attached and fastened on the first rotation rod (31) and the second rotation rod (41), respectively. Accordingly, a plurality of spinous process fixing spikes (32a and 33a) provided in the upper wings (32 and 33) and a plurality of spinous process fixing spikes (42a and 43a) provided in the lower wings (42 and 43) are embedded in the upper spinous process (sp1) and the lower spinous process (sp2). After the interspinous dynamic implant (10) is inserted between the upper and lower spinous processes (sp1 and sp2), the first rotation rod (31) and the second rotation rod (41) are rotated using a separate tool.

Oblong through holes to which the first rotation rod (31) and the second rotation rod (41) are coupled therethrough are formed in the lower portions of the upper wings (32 and 33) and the lower wings (42 and 43), respectively. The plurality of spinous process fixing spikes (32a, 33a, 42a, and 43a) is formed in the upper portions of the upper wings (32 and 33) and the lower wings (42 and 43), respectively. The outer surfaces of the first rotation rod 31 and the second rotation rod (41) are formed to have shapes capable of rotating the upper wings (32 and 33) and the lower wings (42 and 43) coupled to the first rotation rod (31) and the second rotation rod (41) through the first rotation rod (31) and the second rotation rod (41).

Referring to FIGS. 17 and 18, an oblong through hole (32b) is formed in the lower portion of the upper wing (32), and the plurality of spinous process fixing spike (32a) is provided in the lower portion of the upper wing (32). The remaining wings have the same configuration as the upper wing (32). Screw threads are formed in the outer surface of the first rotation rod (31) and combined with a nut. Both sides of the first rotation rod (31) are cut off in such a manner that the oblong through hole (32b) formed in the upper wing (32) is well combined with the first rotation rod (31). When the first rotation rod (31) is rotated, the upper wing (32) is also rotated.

Referring to FIGS. 13 and 14, the through hole (21a) formed to penetrate the side of the upper plate (21) and the through hole (22a) formed to penetrate the side of the lower plate (22) are formed at mutually dislocated locations. The first rotation rod (31) is provided more on the front side than the second rotation rod (41). By rotating the first rotation rod (31) and the second rotation rod (41) in the same direction using a separate tool, the upper wings (32 and 33) combined with the first rotation rod (31) are upward rotated and the lower wings (42 and 43) combined with the second rotation rod (41) are downward rotated.

The through hole (21a) formed in the upper plate (21) and the through hole (22a) formed in the lower plate (22) are formed at the locations where the through hole (21a) and the through hole (22a) do not overlap. Accordingly, the thickness of the spacer (20) can be prevented from being excessively increased, and the first rotation rod (31) and the second rotation rod (41) can be smoothly rotated without being mutually influenced.

Referring to FIG. 5, when the interspinous dynamic implant is inserted between the adjacent spinous processes (sp1 and sp2), one ends of the upper wings (32 and 33) coupled to the first rotation rod (31) and one ends of the lower wings (42 and 43) coupled to the second rotation rod (41) have been folded in opposite directions.

Referring to FIG. 6, when the first rotation rod (31) and the second rotation rod (41) are rotated using a tool, the folded upper wings (32 and 33) are upward rotated and the folded lower wings (42 and 43) are downward rotated and spread.

Referring to FIGS. 2 to 4, the first rotation rod (31) and the second rotation rod (41) are bolt forms. A bolt head (34, 44) is located on one side of the upper plate (21), the lower plate (22). A bolt body (31, 41) is exposed to the other side of the upper plate (21), the lower plate (22) through the through hole (21a, 22a). A left wing (32) forming an upper wing is coupled to the bolt body (31) exposed between the bolt head (34) and the upper plate (21). A left wing (42) forming a lower wing is coupled to the bolt body (41) exposed between the bolt head (44) and the lower plate (22). A right wing (33) forming an upper wing and a right wing (43) forming a lower wing are coupled to the bolt bodies (31 and 41) exposed to the other side.

Referring to FIG. 17, the outer surface of the bolt body (31) that corresponds to a portion combined with the oblong through hole (32b) formed in the left wing (32, 42) and the right wing (33, 43) includes a plurality of faces (31a and 31b) that is flat cut so that the left, right wing is rotated when the bolt body is rotated. The second rotation rod (41) also has the same configuration as the first rotation rod (31).

More specifically, part of the outer surface of the bolt body corresponding to the portion (31a) that belongs to the bolt body (31) and to which the left wing (32, 42) is coupled has been flat cut so that the bolt body can rotate the left wing penetrating the bolt body. Part (31c) of the bolt body extended from the portion to which the left wing (32, 42) is coupled forms a cylindrical body. Part of the outer surface of the bolt body corresponding to the portion (31b) to which the right wing (33, 43) is coupled has been flat cut so that the bolt body can rotate the right wing penetrating the bolt body.

Referring to FIGS. 8 to 10, after the interspinous dynamic implant (10) is inserted between the adjacent spinous processes (sp1 and sp2), it rotates the first rotation rod (31) and the second rotation rod (41) to upward rotate the upper wings (32 and 33) and to downward rotate the lower wings (42 and 43). In this case, the lower wings (42 and 43) may be first downward rotated earlier than the upper wings (32 and 33).

Fastening nuts (35 are 45) are coupled to the outer bolt bodies (31 and 41) of the right wings (33 and 43). The right wing (33) moves in the direction of the left wing (32) along the bolt body (31) by fastening the fastening nut (35) coupled to the first rotation rod (31). When the right wing

(33) comes into contact with the side of the upper plate (21) and no longer moves, if the fastening nut (35) continues to be rotated and fastened, the left wing (32) also moves in the direction of the right wing (33) along the bolt body (31), so the left wing (32) is also closely attached to the side of the upper plate (21).

Furthermore, the right wing (43) moves in the direction of the left wing (42) along the bolt body (41) by fastening the fastening nut (45) coupled to the second rotation rod (41). When the right wing (43) comes into contact with the side of the lower plate (22) and no longer moves, if the fastening nut (45) continues to be fastened, the left wing (42) also moves in the direction of the right wing (43) along the bolt body (41), so the left wing (42) is also closely attached to the lower plate (22).

As a result, the left wing (32) and the right wing (33) that form the upper wings are closely attached and mutually fastened in the direction in which they face each other. The left wing (42) and the right wing (43) that form the lower wings are closely attached and fastened in the direction in which they face each other.

Furthermore, after the left and right wings (32 and 33) are closely attached and fastened by the fastening nut (35), a fixing nut (36) is coupled to the outer bolt body (31) of the fastening nut (35). After the left and right wings (42 and 43) are closely attached and fastened by the fastening nut (45), a fixing nut (46) is coupled to the outer bolt body (41) of the fastening nut (45). By firmly combining and fixing the fixing nuts (36 and 46), a task for inserting the interspinous dynamic implant (10) between the adjacent spinous processes (sp1 and sp2) and coupling the interspinous dynamic implant (10) thereto is completed.

Meanwhile, one or more osseointegration holes (23) are formed in at least one of the upper plate (21) and the lower plate (22) so that the at least one plate is fused with the adjacent spinous processes (sp1 and sp2). A plurality of fixing protrusion (25) is formed in at least one of the top surface of the upper plate (21) and the bottom surface of the lower plate (22) so that the fixing protrusion (25) are coupled to the adjacent spinous processes (sp1 and sp2).

In accordance with the present invention, there are advantages in that the space between the upper spinous process and the lower spinous process can be maintained because an elastic force is provided to the upper spinous process and the lower spinous process and a phenomenon in which the interspinous dynamic implant escapes between the upper spinous process and the lower spinous process can be prevented without damaging the spinous process because the implant is fused with the upper and lower spinous processes and moved therewith.

Furthermore, there are advantages in that a movement of the upper spinous process and the lower spinous process is more natural than that of a conventional implant and there is no burden on the spine because the implant can move along with an upward or downward or leftward or rightward movement of adjacent spinous processes.

Furthermore, there is an advantage in that a minimum invasion procedure is possible because the wings are rotated and fastened using a tool after the interspinous dynamic implant is inserted from the sides of the spinous processes.

Furthermore, there is an advantage in that the upper wing and the lower wing are stably coupled to the upper and lower spinous processes because the plurality of spikes included in the upper and lower wings are closely attached to both sides of the upper and lower spinous processes and embedded therein when the upper and lower wings are fastened on both sides of the upper and lower spinous processes after the interspinous dynamic implant is inserted between the adjacent spinous processes.

Furthermore, there is an advantage in that the interspinous dynamic implant can be inserted from the sides of the spinous processes as well as at the back of the spinous processes because the implant can be inserted between the spinous processes in the state in which the upper wing and the lower wing have been folded and thus the wings are not caught in the upper and lower spinous processes.

The present invention is not limited to the specific and preferred embodiment, and a person having ordinary skill in the art to which the present invention pertains may modify the present invention in various ways without departing from the gist of the present invention claimed in the claims. It is evident that such changes fall in the range of the writing of the claims.

We claim:

1. An interspinous dynamic implant inserted between an upper spinous process and a lower spinous process, the implant comprising:
    an upper plate;
    a lower plate disposed below the upper plate;
    a movable unit coupled between a front portion of the upper plate and a front portion of the lower plate to enable the upper plate and the lower plate to move upward or downward or leftward or rightward within a specific range in response to a movement of the spinous process;
    upper spinous process coupling device closely coupling the upper plate to the upper spinous process; and
    lower spinous process coupling device closely coupling the lower plate to the lower spinous process,
    wherein:
    the upper spinous process coupling device is coupled to the upper plate, upward rotated, and then coupled to the upper, upward rotated, and then coupled to the spinous process, and
    the lower spinous process coupling device is coupled to the lower plate, downward rotated, and then coupled to the lower spinous process.

2. The interspinous dynamic implant of claim 1, wherein one or more osseointegration holes are formed in at least one of the upper plate and the lower plate so that the at least one plate is fused with adjacent spinous processes.

3. The interspinous dynamic implant of claim 1, wherein a plurality of fixing protrusions is formed in at least one of a top surface of the upper plate and a bottom surface of the lower plate so that the fixing protrusions are fused with adjacent spinous processes.

4. The interspinous dynamic implant of claim 1, wherein:
    the upper spinous process coupling device is upward rotated by a first rotation rod inserted into a through hole formed to penetrate a side of the upper plate and rotated with the upper plate, and coupled to the upper spinous process, and
    the lower spinous process coupling device is downward rotated by a second rotation rod inserted into a through hole formed to penetrate a side of the lower plate and rotated with the lower plate, and coupled to the lower spinous process.

5. The interspinous dynamic implant of claim 4, wherein:
    an upper wing coupled to the first rotation rod through the first rotation rod is upward rotated,
    a lower wing coupled to the second rotation rod through the second rotation rod is downward rotated, and the upper wing and the lower wing are closely attached and mutually fastened on the first rotation rod and the second rotation rod, respectively, so a plurality of spinous process fixing spikes provided in the upper wing and a plurality of spinous process fixing spikes provided in the lower wing are embedded in the upper spinous process and the lower spinous process.

6. The interspinous dynamic implant of claim 5, wherein:
the through hole formed to penetrate the side of the upper plate and the through hole formed to penetrate the side of the lower plate are formed at mutually dislocated locations so that the first rotation rod is provided more on a front side than the second rotation rod, and
the upper wing coupled to the first rotation rod is upward rotated and the lower wing coupled to the second rotation rod is downward rotated by rotating the first rotation rod and the second rotation rod in an identical direction.

7. The interspinous dynamic implant of claim 5, wherein:
oblong through holes to which the first rotation rod and the second rotation rod are coupled through the oblong through holes are formed on lower sides of the upper wing and the lower wing, respectively,
a plurality of spinous process fixing spikes is provided on an upper side of each of the upper wing and the lower wing, and
outer surfaces of the first rotation rod and the second rotation rod are formed in shapes capable of rotating the upper wing and the lower wing coupled to the first rotation rod and the second rotation rod through the first rotation rod and the second rotation rod.

8. The interspinous dynamic implant of claim 5, wherein:
the first rotation rod and the second rotation rod have bolt forms,
a bolt head is located on one side of each of the upper plate and the lower plate,
a bolt body is exposed to the other side through the through hole,
a left wing forming the upper wing is coupled to a bolt body exposed between the bolt head and the upper plate,
a left wing forming the lower wing is coupled to a bolt body exposed between the bolt head and the lower plate, and
the right wing forming the upper wing and the right wing forming the lower wing are coupled to the bolt body exposed to the other side.

9. The interspinous dynamic implant of claim 8, wherein outer surfaces of the bolt bodies corresponding to portions coupled to the oblong through holes formed in the left wing and the right wing comprise a plurality of faces flat cut in such a way as to rotate the left and right wings when the bolt bodies are rotated.

10. The interspinous dynamic implant of claim 8, wherein:
a fastening nut is coupled to an outer bolt body of the right wing, and
when the fastening nut is fastened, the right wing moves in a direction of the left wing along the bolt body and the left wing moves in a direction of the right wing along the bolt body, so the left wing and the right wing are closely attached and fastened in a direction in which the left wing and the right wing face each other.

11. The interspinous dynamic implant of claim 10, wherein after the left and right wings are closely attached and fastened by the fastening nut, a fixing nut is coupled to an outer bolt body of the fastening nut.

12. An interspinous dynamic implant inserted between an upper spinous process and a lower spinous process, the implant comprising:
an upper plate;
a lower plate disposed below the upper plate;
a movable unit coupled between a front portion of the upper plate and a front portion of the lower plate to enable the upper plate and the lower plate to move upward or downward or leftward or rightward within a specific range in response to a movement of the spinous process, wherein the movable unit comprises:
a cushion unit of an elastic material which is located between the upper plate and the lower plate, which has a circular through hole formed at a center of the cushion unit, and which has side portions closely attached to both sides of the upper plate and the lower plate; and
a coupling unit of a dumbbell shape which couples the upper plate, the cushion unit and the lower plate sequentially through a through hole formed to penetrate the upper plate from a top surface of the front portion of the upper plate to a bottom surface, a through hole formed in the cushion unit of the elastic material, and a through hole formed to penetrate the lower plate from a top surface of the front portion of the lower plate to a bottom surface.

13. The interspinous dynamic implant of claim 12, wherein the cushion unit of the elastic material has an H form.

14. The interspinous dynamic implant of claim 12, wherein:
the coupling unit of the dumbbell shape comprises a body unit located at a center of the coupling unit, a first coupling unit coupled to the through hole formed in the upper plate, and a second coupling unit coupled to the through hole formed in the lower plate,
an outer surface of each of the first coupling unit and the second coupling unit has a diameter increasing from the body unit to an outside, but forms a convex surface, and
the through holes formed in the upper plate and the lower plate are formed to correspond to respective shapes corresponding to the first coupling unit and the second coupling unit.

* * * * *